United States Patent
Martin

(10) Patent No.: US 11,504,411 B1
(45) Date of Patent: Nov. 22, 2022

(54) HERBAL DIETARY SUPPLEMENT SUPPORTING HEALTHY IMMUNE FUNCTION

(71) Applicant: Progressing Bodies, Inc., Mableton, GA (US)

(72) Inventor: Geovon K Martin, Mableton, GA (US)

(73) Assignee: Progressing Bodies, Inc., Mableton, GA (US)

( * ) Notice: Subject to any disclaimer, the term of this patent is extended or adjusted under 35 U.S.C. 154(b) by 0 days.

(21) Appl. No.: 17/741,793

(22) Filed: May 11, 2022

Related U.S. Application Data

(60) Provisional application No. 63/190,015, filed on May 18, 2021.

(51) Int. Cl.
| | | |
|---|---|---|
| *A61K 36/9066* | (2006.01) | |
| *A61K 36/185* | (2006.01) | |
| *A61K 36/481* | (2006.01) | |
| *A61K 36/28* | (2006.01) | |
| *A61K 36/31* | (2006.01) | |
| *A61P 37/04* | (2006.01) | |
| *A61K 31/714* | (2006.01) | |
| *A61K 31/355* | (2006.01) | |
| *A61K 36/8962* | (2006.01) | |
| *A61K 36/53* | (2006.01) | |
| *A61K 31/122* | (2006.01) | |

(52) U.S. Cl.
CPC ........ *A61K 36/9066* (2013.01); *A61K 31/122* (2013.01); *A61K 31/355* (2013.01); *A61K 31/714* (2013.01); *A61K 36/185* (2013.01); *A61K 36/28* (2013.01); *A61K 36/31* (2013.01); *A61K 36/481* (2013.01); *A61K 36/53* (2013.01); *A61K 36/8962* (2013.01); *A61P 37/04* (2018.01)

(58) Field of Classification Search
None
See application file for complete search history.

(56) References Cited

U.S. PATENT DOCUMENTS

| | | |
|---|---|---|
| 2011/0020443 A1 | 1/2011 | Liu et al. |
| 2018/0273517 A1 | 9/2018 | Patron et al. |
| 2020/0384055 A1 | 12/2020 | Schirle |
| 2020/0396961 A1 | 12/2020 | Zetouna |

OTHER PUBLICATIONS

Journal of the American College of Cardiology, vol. 46, Issue 1, Jul. 2005, pp. 184-221.*
Erowele GI, Kalejaiye AO. Pharmacology and therapeutic uses of cat's claw. Am J Health Syst Pharm. Jun. 1, 2009;66(11):992-5. doi: 10.2146/ajhp080443. PMID: 19451609.
Lamm S, Sheng Y, Pero RW. Persistent response to pneumococcal vaccine in individuals supplemented with a novel water soluble extract of Uncaria tomentosa, C-Med-100. Phytomedicine. Jul. 2001;8(4):267-74. doi: 10.1078/0944-7113-00046 PMID: 11515716.
Sheng Y, Bryngelsson C, Pero RW. Enhanced DNA repair, immune function and reduced toxicity of C-MED-100, a novel aqueous extract from Uncaria tomentosa. J Ethnopharmacol. Feb. 2000;69(2):115-26. doi: 10.1016/s0378-8741(99)00070-7. PMID: 10687868.
Mullins RJ, Heddle R. Adverse reactions associated with echinacea: the Australian experience. Ann Allergy Asthma Immunol. Jan. 2002;88(1):42-51. doi: 10.1016/S1081-1206(10)63591-0. PMID: 11814277.
Kyo E, Uda N, Kasuga S, Itakura Y. Immunomodulatory effects of aged garlic extract. J Nutr. Mar. 2001; 131(3s):1075S-9S. doi: 10.1093/jn/131.3.1075S. PMID: 11238820.
Borlinghaus J, Albrecht F, Gruhlke MC, Nwachukwu ID, Slusarenko AJ. Allicin: chemistry and biological properties. Molecules. Aug. 19, 2014;19(8):12591-618. doi: 10.3390/molecules190812591. PMID: 25153873 PMCID: PMC6271412.
John R. Whitaker, Development of Flavor, Odor, and Pungency in Onion and Garlic, Editor(s): C.O. Chichester, E.M. Mrak, G.F. Stewart,Advances in Food Research, Academic Press,vol. 22, 1976,pp. 73-133,ISSN 0065-2628, ISBN 9780120164226, https://doi.org/10.1016/S0065-2628(08)60337-7.(https://www.sciencedirect.com/science/article/pii/S0065262808603377).
Porter RS, Bode RF. A Review of the Antiviral Properties of Black Elder (*Sambucus nigra* L.) Products. Phytother Res. Apr. 2017;31(4):533-554. doi: 10.1002/ptr.5782. Epub Feb. 15, 2017. PMID: 28198157.
Zakay-Rones Z, Thom E, Wollan T, Wadstein J. Randomized study of the efficacy and safety of oral elderberry extract in the treatment of influenza A and B virus infections. J Int Med Res. Mar.-Apr. 2004;32(2):132-40. doi: 10.1177/147323000403200205. PMID: 15080016.
Evelin Tiralongo, Shirley S. Wee, Rodney A. Lea. Elderberry Supplementation Reduces Cold Duration and Symptoms in Air-Travellers: A Randomized, Double-Blind Placebo-Controlled Clinical Trial Apr. 2016; 8(4): 182. Published online Mar. 24, 2016. doi: 10.3390/nu8040182
Aguilar JL, Rojas P, Marcelo A, Plaza A, Bauer R, Reininger E, Klaas CA, Merfort I. Anti-inflammatory activity of two different extracts of Uncaria tomentosa (Rubiaceae). J Ethnopharmacol. Jul. 2002;81(2):271-6. doi: 10.1016/s0378-8740(02)00093-4. PMID: 12065162.
Gilling DH, Kitajima M, Torrey JR, Bright KR. Antiviral efficacy and mechanisms of action of oregano essential oil and its primary component carvacrol against murine norovirus. J Appl Microbiol. May 2014;116 (5):1149-63. doi: 10.1111/jam.12453. Epub Feb. 12, 2014. PMID: 24779581. .

(Continued)

*Primary Examiner* — Michael V Meller
(74) *Attorney, Agent, or Firm* — Fennemore Craig, P.C.

(57) ABSTRACT

An herbal formulation including effective amounts of cat's claw extract, *Astragalus* extract, *Echinacea* extract, *Moringa* extract; astaxanthin, black elderberry extract, vitamin B12, blackseed extract, oregano extract; garlic extract; tumeric extract, and vitamin E provides nutritional support for healthy immune function. The herbal formulation may be packaged in dosage forms that are particularly effective in fighting infections, and especially viral infections.

16 Claims, No Drawings

(56) References Cited

OTHER PUBLICATIONS

Hilepo JN, Bellucci AG, Mossey RT. Acute renal failure caused by 'cat's claw' herbal remedy in a patient with systemic lupus erythematosus. Nephron. 1997;77(3):361. doi: 10.1159/000190304. PMID: 9375835.

Flythe JE, Rueda JF, Riscoe MK, Watnick S. Silicate nephrolithiasis after ingestion of supplements containing silica dioxide. Am J Kidney Dis. Jul. 2009;54(1):127-30. doi: 10.1053/j.ajkd.2008.10.042. Epub Dec. 19, 2008. PMID: 19100669.

Styczynski J, Wysocki M. Alternative medicine remedies might stimulate viability of leukemic cells. Pediatr Blood Cancer. Jan. 2006;46(1):94-8. doi: 10.1002/pbc.20513. PMID: 16047362.

Nahida Tabassum, Feroz Ahmad. Department of Pharmaceutical Sciences, University of Kashmire, Hazratbal, Srinager, J&K-190 006, India. Role of natural herbs in the treatment of hypertension. Pharmacogn Rev. Jan.-Jun. 2011; 5(9): 30-40.doi: 10.4103/0973-7847.79097.

M.B. Fasano. Allergenic Cross-Reactivity between Echinacea and Ragweed DOI:https://doi.org/10.1016/j.iaci.2006.12.428.

Lai WL, Chuang HS, Lee MH, Wei CL, Lin CF, Tsai YC. Inhibition of herpes simplex virus type 1 by thymol-related monoterpenoids. Planta Med. Oct. 2012;78(15):1636-8. doi: 10.1055/s-0032-1315208. Epub Aug. 13, 2012. PMID: 22890541.

International Search Report and Written Opinion, dated Aug. 2, 2022, for International Application No. PCT/US22/28743, dated May 11, 2022, 7 pages.

Rosenbaum "Antioxidants and Antiinflammatory Dietary Supplements for Osteoartritis and Rheumatoid Arthritis" 32-40. Alternative Therapies in Heath and Medicine. Apr. 2010; Entire Document.

\* cited by examiner

HERBAL DIETARY SUPPLEMENT SUPPORTING HEALTHY IMMUNE FUNCTION

CROSS-REFERENCE TO RELATED APPLICATION

This application claims the benefit of U.S. Provisional Patent Application No. 63/190,015, filed on May 18, 2021, which is hereby incorporated herein by reference for all that it discloses.

TECHNICAL FIELD

The present invention relates to the field of herbal supplements in general and more particularly to herbal supplements supporting healthy immune functions.

BACKGROUND

A body of knowledge exists for herbalists concerning plant materials and extractions from plant materials and intended benefits to people who consume formulations of these materials. This body of knowledge may sometimes date back hundreds or even thousands of years. Herbal supplements are sometimes studied using clinical methods that either confirm or reject the presumed effects but, in context of the art as a whole, the body of knowledge has arisen in historical contexts that are separate and apart from modern scientific methods, such as controlled clinical studies.

Generally speaking, the body of herbal knowledge extends into a variety of plants and extracts that are believed to support healthy immune function. Echinacea (*Echinacea angustafolia*) is perhaps the most commonly used immune-boosting plant material. *Echinacea* and extracts thereof have been shown to improve immunity, blood sugar, anxiety, inflammation, and skin health. It may even have anti-cancer properties. However, human-based research is often limited. *Echinacea* considered safe and well tolerated for short-term use. Suggested dosages vary depending on the particular form of *Echinacea* being used. Although *Echinacea* is commonly used to treat the common cold, results in this area are mixed. While research has shown that *Echinacea* may help prevent colds, shorten their duration, or provide symptomatic relief, many studies have been poorly designed or show no real benefit.

Although *Echinacea* products appear to be safe and well-tolerated for short-term use, the art does note a number of potential side effects. These include rashes, itchy skin, hives, swelling, stomach pain, nausea, and shortness of breath. These side effects are more common among people with allergies to other flowers, such as daisies, chrysanthemums, marigolds, and ragweed.

Cat's claw (*Uncaria tomentosa*) is less commonly used. Cat's claw is a tropical vine that can grow up to 98 feet (30 meters) tall. Cat's claw has been used for centuries as a traditional medicine. Cat's claw is believed to may support the immune system, possibly helping to fight infections more effectively. A small study in 27 men found that consuming 700 mg of cat's claw extract for 2 months increased their number of white blood cells, which are involved in combating infections. Another small study in four men given cat's claw extract for six weeks noted the same results. The effect of using cat's claw is, however, uncertain because the material is believed to both boost the immune system and calm an overactive immune system. It has not been established whether this is a dosing phenomenon or the result of anti-inflammatory properties that may also inure to cat's claw.

While side effects of cat's claw are rarely reported, its safety has not been extensively studied-particularly in a context where cat's claw is used in combination with other materials. Problematically, the high levels of tannins in cat's claw may cause some side effects including nausea, stomach upset, and diarrhea if the material is consumed in large amounts. Case reports and test-tube studies support other possible side effects, including low blood pressure, increased risk of bleeding, nerve damage, anti-estrogen effects, and adverse effects on kidney function. That said, these symptoms are rare.

Still, certain people are discouraged from taking cat's claw. Cat's claw is not considered safe to take during pregnancy or breast-feeding due to a lack of safety information. Those with bleeding disorders, autoimmune disease, kidney disease, leukemia, problems with blood pressure, or who are awaiting surgery should avoid cat's claw, as should people with certain medical conditions. Cat's claw may also interfere with some drugs, such as those for blood pressure, cholesterol, cancer, and blood clotting.

Astragalus (*Astragalus propinquss*) is another herb that may have immune boosting effects. *Astragalus* is a herbaceous perennial plant of the pea family and is sometimes used for immune enhancement. Most research on *Astragalus* has focused on its immuno-stimulatory activity and its seemingly remarkable ability to restore the activity of a suppressed immune system. Clinical trials as well as pharmacological data provide evidence for the usefulness of *Astragalus* in the prevention of the common cold and as an adjunct to cancer therapies. *Astragalus* is may be useful as a complementary treatment during chemotherapy, radiation therapy and immune deficiency syndromes.

Moringa (*Moringa oleifera*) is an edible plant that is native to areas of India, Pakistan, Bangladesh, and Afghanistan. It is also grown in the tropics. The leaves, bark, flowers, fruit, seeds, and root are used to make medicine. Herbalists use *Moringa* against for asthma, diabetes, obesity, symptoms of menopause, and other conditions. A little-known superfood in the West, *Moringa* has many important vitamins and minerals. The leaves have 7 times more vitamin C than oranges and 15 times more potassium than bananas. *Moringa* also has calcium, protein, iron, and amino acids. *Moringa* possesses antibacterial, antifungal, and antimicrobial properties, and is effective against the growth of disease-causing microbes. Scientific research has proven that *Moringa* extracts exert a wide spectrum of protective activity against food-borne microorganisms such as *Salmonella, Rhizopus* species, *E. Coli, Enterobacter aerogenes, Pseudomonas aeruginosa*, and *Staphylococcus aureus*. This defensive activity makes its extracts perfect for sanitation and preservation purposes. Leaves of this plant possess antifungal qualities. The inhibitory effects of *Moringa* help in preventing the growth of contaminant fungi such as *Aspergillus* spp. and *Penicillium* spp.

The extracts of *Moringa* seeds possess anti-allergenic qualities, such that *Moringa* plant extracts may provide relief from bronchial asthma and inflammation of the airways. Extracts of *Moringa* may be useful against certain hypersensitive reactions involved in various allergic diseases, including allergic rhinitis and anaphylaxis. The use of *Moringa* reduces the severity of asthmatic attacks and various symptoms such as wheezing, cough, dyspnea, and contraction of the chest be reducing the histamine release response from mast cells in the immune system. *Moringa* is believed to protect against bronchial constrictions and encourages better lung function and respiration.

Black elderberry (*Sambucus nigra*) is one of the most commonly used medicinal plants in the world. Traditionally, indigenous people used elderberry to treat fever and rheumatism, while the ancient Egyptians used elderberry to improve their complexions and heal burns. Elderberry is still used in folk medicine across many parts of Europe. Today, elderberry is most often taken as a supplement to treat cold and flu symptoms. Black elderberry extracts and flower infusions have been shown to help reduce the severity and length of influenza. Commercial preparations of elderberry for the treatment of colds come in various forms, including liquids, capsules, lozenges, and gummies.

Certain studies confirm the effectiveness of elderberry. One 2004 study of 60 people with influenza found that those who took 15 ml. of elderberry syrup four times per day showed symptom improvement in 2 to 4 days, while the control group took 7 to 8 days to improve. Another study of 312 air travelers taking capsules containing 300 mg. of elderberry extract three times per day found that those who got sick experienced a shorter duration of illness and less severe symptoms.

Other supplements including vitamin B12 and folic acid enhance the production of red blood cells that carry oxygen around the body. A lack of vitamin B12 in one's diet can lead to pernicious anemia, which is an autoimmune disorder that causes the immune system to attack stomach cells. This instigates a vicious cycle by inhibiting the body's ability to absorb vitamin B12.

Blackseed extract (*Nigella sativa*) may be used against asthma and allergies. According to a 2013 review investigating the therapeutic potential of *Nigella sativa* in boiled extract form, authors concluded that the natural substance has potential to alleviate the symptoms of asthma by widening the bronchioles to allow airflow to the lungs. Similarly, a month-long 2011 study looked at *Nigella sativa*'s impact on allergic rhinitis. In this sample of 66 men and women who experienced nasal congestion, runny and itchy nose, and sneezing, *Nigella sativa* reduced symptoms during the first two weeks.

Oregano extract (*Origanum vulgare*) may be used against both bacterial and viral infections. Oregano contains carvacrol and thymol, which are associated with antiviral properties. In one test-tube study, carvacrol inactivated norovirus, a viral infection that causes diarrhea, nausea, and stomach pain, and this occurred over the course of less than one hour. Another test-tube study found that thymol and carvacrol inactivated 90% of the herpes simplex virus within just one hour.

Garlic extract may boost immune function. Certain compounds in garlic are believed to help the immune system fight germs. Whole garlic contains a compound called allicin. When garlic is crushed or chewed, this compound turns into allicin, the main active ingredient in garlic. Allicin contains sulfur, which gives garlic its distinctive smell and taste. However, allicin is unstable so it quickly converts to other sulphur-containing compounds thought to give garlic its medicinal properties. These compounds have been shown to boost the disease-fighting response of some types of white blood cells in the body when they encounter viruses, such as the viruses that cause the common cold or flu. Certain studies suggest that garlic reduces the risk of becoming sick in the first place, as well as how long you stay sick. It can also reduce the severity of symptoms. One study gave 146 healthy volunteers either garlic supplements or a placebo for three months. The garlic group had a 63% lower risk of getting a cold, and their colds were also 70% shorter. Another study found that colds were on average 61% shorter for subjects who ate 2.56 grams of aged garlic extract per day, compared to a placebo group. Their colds were also less severe. These results are uncertain where one review of the evidence found that many of the studies investigating the effects of garlic on the common cold were of poor quality.

Tumeric extract, also known as curcumin extract, may have immune-balancing properties that are helpful to those with chronic stress. Additionally, curcumin may help promote optimal immune responses through its prebiotic-like properties, omega-3 boosting ability, and cortisol-lowering effects.

Vitamin E is a potent antioxidant having also an ability to modulate immune functions. In individuals deficient in vitamin E, most of the immune parameters show a downward trend, which is associated with increased infectious diseases and the incidence of tumors. In contrast, vitamin E supplementation has various beneficial effects on the immune system. The decreased cellular immunity with aging or during the development of AIDS is markedly improved by the intake of a high vitamin E diet. In addition, vitamin E plays an important role in the differentiation of immature T cells in thymus. Vitamin E deficiency induces the decreased differentiation of immature T cells, which results in the early decrease of cellular immunity with aging in spontaneously hypertensive rats. Conversely, vitamin E supplementation induces a higher differentiation of immature T cells via increased positive selection by thymic epithelial cells, which results in the improvement of decreased cellular immunity in the aged.

Furthermore, vitamin E supplementation induces the early recovery of thymic atrophy following X-ray irradiation. Taken together, these results suggest that vitamin E is an important nutrient for maintaining the immune system, especially in the aged.

Astaxanthin (*Haematococcus pluvialis*), an algae high in antioxidants, provides antioxidant material that protects both the fat-soluble and the water-soluble parts of cells. Most antioxidants only protect one or the other, but astaxanthin can span the cell membrane such that tone part of the antioxidant resides in the fat-soluble part of the cell and another end resides in the water-soluble part. This protects the entire cell. Astaxanthin has been experimentally confirmed to be what is regarded as the very strongest natural antioxidant. For example, in singlet oxygen quenching, astaxanthin ranges from 550 times stronger than green tea catechins to 800 times stronger than CoQ10 to an incredible 6,000 times stronger than vitamin C.

SUMMARY OF THE INVENTION

One embodiment of an herbal formulation for supporting healthy immune system function may include effective amounts of: cat's claw extract; *Astragalus* extract; *Echinacea* extract; *Moringa* extract; astaxanthin; black elderberry extract; vitamin B12; blackseed extract; oregano extract; garlic extract; tumeric extract; and vitamin E.

In another embodiment, the herbal formulation may include cat's claw extract in an amount ranging from 4.7-7.0 percent by weight; *Astragalus* extract in an amount ranging from 4.7-7.0 percent by weight; *Echinacea* extract in an amount ranging from 4.6-6.9 percent by weight; *Moringa* extract in an amount ranging from 14.8-22.2 percent by weight; astaxanthin in an amount ranging from 0.31-0.46 percent by weight; black elderberry extract in an amount ranging from 4.3-6.5 percent by weight; vitamin B12 in an amount ranging from 8.0-12.0 percent by weight; blackseed extract in an amount ranging from 3.1-4.6 percent by weight; oregano extract in an amount ranging from 4.6-6.9 percent by weight; garlic extract in an amount ranging from 9.3-13.9 percent by weight; tumeric extract in an amount ranging from 3.9-4.5 percent by weight; and vitamin E in an amount ranging from 18.5-27.8 percent by weight.

Also disclosed are dosage forms of the herbal formulation and methods of providing immune system support by administering the dosage forms at various intervals upon exposure to an infectious agent or upon development of symptoms of an infection.

DETAILED DESCRIPTION OF THE PREFERRED EMBODIMENTS

There will now be shown and described, by way of non-limiting examples, various instrumentalities for overcoming the problems discussed above. The instrumentalities disclosed herein overcome the problems outlined above and advance the art by providing an herbal formulation that, with proper dosages, offers a surprisingly high level of immune system support. The herbal formulations combine a plurality of agents that are known to boost the immune system. Powerful antioxidants are also combined to provide additional immune support that is particularly effective when the body of an infected individual is fighting an active infection. Overall, the combined ingredients have a broad-spectrum effect against many types of bacterial and viral infections. Results that have been achieved against viral infections are surprisingly good.

Unless defined otherwise, all technical and scientific terms used herein have the same meaning as commonly understood by persons having ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, a relief from symptoms, as determined by any means suitable in the art.

Ranges: Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1-10 should be considered to have specifically disclosed sub-ranges such as from 1-3, from 1-4, from 1-5, from 2-4, from 2-5, from 2-8, from 3-9, etc., as well as individual numbers within that range, for example, 1, 2, 2.4, 2.7, 3, 3.6, 4, 5, 5.8, and 10. This applies regardless of the breadth of the range.

The herbal formulations include a plurality of herbal materials, including plant material and extracts, that provide nutritional support for broad-spectrum immune system enhancement, together with a broad range of antioxidants. The table below provides a listing of these ingredients according to a range of concentrations and relative weights that are suitable for use in a dosage formulation.

TABLE

HERBAL FORMULATION CONTENT

| Material | Suitable (wt. %) | Preferred (wt. %) | Most Preferred (wt. %) | Exemplary Single Dose* Content (mg) |
|---|---|---|---|---|
| Cat's Claw Extract 20:1 (*uncaria tomentosa*) | 4.7-7.0 | 5.3-6.5 | 5.6-6.2 | 76 |
| Astragalus Extract 20:1 (*astragalus propinquss*) | 4.7-7.0 | 5.3-6.5 | 5.6-6.2 | 76 |
| Echinacea Extract 4:1 (*echinacea angustafolia*) | 4.6-6 . 9 | 5.1-6.3 | 5.4-6.0 | 74 |
| Moringa Extract 20:1 (*moringa oleifera*) | 14.8-22.2 | 16.7-20.4 | 17.6-19.5 | 240 |
| Astaxanthin (*haematococcus pluvialis*) | 0.31-0.46 | 0.35-0.42 | 0.37-0.41 | 5 |
| Black Elderberry Extract (*sambucus nigra*) | 4.3-6.5 | 4.9-5.9 | 5.1-5.7 | 70 |
| Vitamin B12 | 8.0-12.0 | 9.0-11.0 | 9.5-10.5 | 130 |
| Blackseed Extract (*nigella sativa*) | 3.1-4.6 | 3.5-4.2 | 3.7-4.1 | 50 |
| Oregano Extract (*origanum vulgare*) | 4.6-6.9 | 5.2-6.4 | 5.5-6.1 | 75 |
| Garlic Extract | 9.3-13.9 | 10.4-12.7 | 11.0-12.2 | 150 |
| Tumeric Extract | 3.9-4.5 | 3.4-4.2 | 3.6-4.0 | 49 |
| Vitamin E | 18.5-27.8 | 20.8-25.5 | 22.0-24.3 | 300 |
| Total | | | | 1295 |

*To assist the body in fighting active infection

In some embodiments, vitamin E may be provided as D-alpha-tocopheryl succinate, a natural and highly effective form of vitamin E.

The foregoing ingredients may be combined into a dosage form using standard procedures known to the art for making a pill, capsule, or edible material, such as a gummy treat. The herbal formulation may also contain conventional food supplement fillers and extenders, if desired. The herbal formulation may be taken orally. A suitable dosage range is, for example, from about 3.6 mg/kg of body weight to about 10.6 mg/kg of body weight, taken three times a day after an individual is either exposed to an infectious agent or is initially becoming symptomatic to an infection. This amounts to a dosage of from about 650 mg to about 1950 mg for a person of average weight. A more preferred dosage range for this use is from about 5.1 mg/kg of body weight to about 9.4 mg/kg of body weight, taken three times a day, which is from about 910 mg to about 1590 mg for a person of average weight. The most preferred dosage range for this use is about 7.2 mg/kg of body weight taken three times a day or about 1300 mg for a person of average weight. Optionally, an initial double dosage (i.e., two of any of these dosages) may be administered to an individual after the individual has either been exposed to an infectious agent or has become symptomatic.

These dosages may be halved and taken once a day for maintenance or prophylactic support of healthy immune function. For example, a maintenance dosage suitably includes a dosage of about 1.8 mg/kg of body weight to about 5.3 mg/kg of body weight taken once a day, which amounts to from about 325 mg to about 975 mg for a person of average weight. A more preferred maintenance dose is from about 2.5 mg/kg of body weight to about 4.7 mg/kg of body weight taken once a day, which is from about 455 mg to about 855 mg for a person of average weight. The most preferred maintenance dosage range for this use is about 3.6 mg/kg of body weight taken once a day, or about 650 mg for a person of average weight.

It will be appreciated from a review of these numbers that any type of dosage form may contain half of the desired dosage for fighting an active infection because this amount taken once a day for maintenance is half of the dosage taken three times a day when the body is fighting an active infection or has been exposed to an infection. A individual may, accordingly, take a single dose form for maintenance over a period of at least several days and two dosages at other times in the case of active infection.

WORKING EXAMPLES

Influenza: A plurality of individuals are administered the exemplary formulation shown in the Table above over an extended period of time. The formulation is administered to each individual immediately upon the individual becoming symptomatic for infection by the influenza virus, these symptoms including fever, body aches, chills, muscle weakness. In substantially all cases, the individual becomes asymptomatic, and on average this occurs within 6 to 8 hours of the administration. The asymptomatic individuals do, however, for a time continue to cough up extra phlegm and mucus.

COVID: Two work colleagues made a business trip together and worked in an office environment in close proximity to one another over a period of days. Both colleagues became ill and were confirmed by testing to have COVID. One colleague took the exemplary formulation as described in the Table above and became asymptomatic within 48 hours. The other colleague did not take the formulation, was hospitalized and almost died. In my most recent discovery, one person tested positive for COVID and had just about all of the symptoms except for issues with their taste buds. The asymptomatic individual did, however, for a time continue to cough up extra phlegm and mucus.

Prophylactic Use: When taken every day, the above formulation helps prevent an individual from catching the common cold, the flu, and even helps prevent an individual from catching COVID.

Having herein set forth preferred embodiments of the present invention, it is anticipated that suitable modifications can be made thereto which will nonetheless remain within the scope of the invention. The invention shall therefore only be construed in accordance with the following claims:

The invention claimed is:

1. A capsule, pill, or gummy treat herbal formulation consisting essentially of: cat's claw extract; *Astragalus* extract; *Echinacea* extract; *Moringa* extract; astaxanthin; black elderberry extract; vitamin B12; blackseed extract; oregano extract; garlic extract; tumeric extract; and vitamin E.

2. The capsule, pill, or gummy treat herbal formulation of claim 1, wherein the concentration of cat's claw extract ranges from 5.3 weight percent to 6.5 weight percent of said herbal formulation.

3. The capsule, pill, or gummy treat herbal formulation of claim 1, wherein the concentration of *Astragalus* extract ranges from 5.3 weight percent to 6.5 weight percent of said herbal formulation.

4. The capsule, pill, or gummy treat herbal formulation of claim 1, wherein the concentration of *Echinacea* extract ranges from 5.1 weight percent to 6.3 weight percent of said herbal formulation.

5. The capsule, pill, or gummy treat herbal formulation of claim 1, wherein the concentration of *Moringa* extract ranges from 16.7 weight percent to 20.4 weight percent of said herbal formulation.

6. The capsule, pill, or gummy treat herbal formulation of claim 1, wherein the concentration of astaxanthin ranges from 0.35 weight percent to 0.42 weight percent of said herbal formulation.

7. The capsule, pill, or gummy treat herbal formulation of claim 1, wherein the concentration of black elderberry extract ranges from 4.9 weight percent to 5.9 weight percent of said herbal formulation.

8. The capsule, pill, or gummy treat herbal formulation of claim 1, wherein the concentration of vitamin B12 ranges from 9.0 weight percent to 11.0 weight percent of said herbal formulation.

9. The capsule, pill, or gummy treat herbal formulation of claim 1, wherein the concentration of blackseed extract ranges from 3.5 weight percent to 4.2 weight percent of said herbal formulation.

10. The capsule, pill, or gummy treat herbal formulation claim 1, wherein the concentration of oregano extract ranges from 5.2 weight percent to 6.4 weight percent of said herbal formulation.

11. The capsule, pill, or gummy treat herbal formulation of claim 1, wherein the concentration of garlic extract ranges from 10.4 weight percent to 12.7 weight percent of said herbal formulation.

12. The capsule, pill, or gummy treat herbal formulation of claim 1, wherein the concentration of tumeric extract ranges from 3.4 weight percent to 4.2 weight percent of said herbal formulation.

13. The capsule, pill, or gummy treat herbal formulation of claim 1, wherein the concentration of vitamin E ranges from 20.8 weight percent to 25.5 weight percent of said herbal formulation.

14. The capsule, pill, or gummy treat herbal formulation of claim 1 in an oral dosage form that contains from about 650 mg to about 1950 mg of said herbal formulation.

15. The capsule, pill, or gummy treat herbal formulation of claim 1 consisting essentially of from about 325 mg to about 975 mg of said herbal formulation.

16. A capsule, pill, or gummy treat herbal formulation consisting essentially of:
    cat's claw extract in an amount ranging from 4.7-7.0 percent by weight;

*Astragalus* extract in an amount ranging from 4.7-7.0 percent by weight;

*Echinacea* extract in an amount ranging from 4.6-6.9 percent by weight;

*Moringa* extract in an amount ranging from 14.8-22.2 percent by weight;

astaxanthin in an amount ranging from 0.31-0.46 percent by weight;

black elderberry extract in an amount ranging from 4.3-6.5 percent by weight;

vitamin B12 in an amount ranging from 8.0-12.0 percent by weight;

blackseed extract in an amount ranging from 3.1-4.6 percent by weight;

oregano extract in an amount ranging from 4.6-6.9 percent by weight;

garlic extract in an amount ranging from 9.3-13.9 percent by weight;

tumeric extract in an amount ranging from 3.9-4.5 percent by weight; and vitamin E in an amount ranging from 18.5-27.8 percent by weight.

\* \* \* \* \*